(12) United States Patent
Janis

(10) Patent No.: US 6,663,583 B1
(45) Date of Patent: Dec. 16, 2003

(54) ANKLE BRACE

(76) Inventor: Leonard R. Janis, 2772 Plymouth Ave., Columbus, OH (US) 43209

( * ) Notice: Subject to any disclaimer, the term of this patent is extended or adjusted under 35 U.S.C. 154(b) by 0 days.

(21) Appl. No.: 10/228,556

(22) Filed: Aug. 27, 2002

(51) Int. Cl.[7] ............................................. A61F 13/00
(52) U.S. Cl. ........................................................ 602/65
(58) Field of Search .............................. 602/27, 65, 23, 602/5, 1, 61, 60

(56) References Cited

U.S. PATENT DOCUMENTS

| | | | |
|---|---|---|---|
| 3,073,305 A | * | 1/1963 | Biggs, Jr. et al. .............. 602/65 |
| 4,313,433 A | | 2/1982 | Cramer |
| 4,527,556 A | | 7/1985 | Nelson |
| 4,729,370 A | | 3/1988 | Kallassy |
| 4,844,058 A | * | 7/1989 | Vogelbach .................... 602/27 |
| 4,878,504 A | | 11/1989 | Nelson |
| 4,962,768 A | * | 10/1990 | Stromgren et al. ........... 602/27 |
| 5,067,486 A | | 11/1991 | Hely |
| 5,099,860 A | * | 3/1992 | Amrein ....................... 128/882 |
| 5,676,641 A | * | 10/1997 | Arensdorf et al. ............ 602/27 |
| 5,795,316 A | * | 8/1998 | Gaylord ....................... 602/27 |
| 5,833,640 A | * | 11/1998 | Vazquez et al. .............. 602/27 |
| 5,944,678 A | * | 8/1999 | Hubbard ....................... 602/27 |
| 6,117,098 A | * | 9/2000 | Weber et al. .................. 602/27 |

* cited by examiner

*Primary Examiner*—Nicholas D. Lucchesi
*Assistant Examiner*—Huong Q. Pham
(74) *Attorney, Agent, or Firm*—Francis T. Kremblas, Jr.; Kremblas, Foster, Phillips & Pollick

(57) ABSTRACT

A removably mounted brace for supporting the ankle joint comprising a main body portion configured to surround ankle and foot portions of the wearer and connecting means for drawing the opposing side sections in a close-fitting snug relationship to the underlying foot and ankle portions of the wearer. A plurality of straps are included which have one end fixed to a side section and a free end. Upon fixing these straps in a manner wherein at least one applies forces in primarily a horizontal direction from the rear and others apply forces in primarily a vertical direction upward from the arch of the foot, they cooperate to maintain the tibia, fibula in their anatomically correct relationship with the talus and resist under forces in both horizontal and vertical directions.

3 Claims, 8 Drawing Sheets

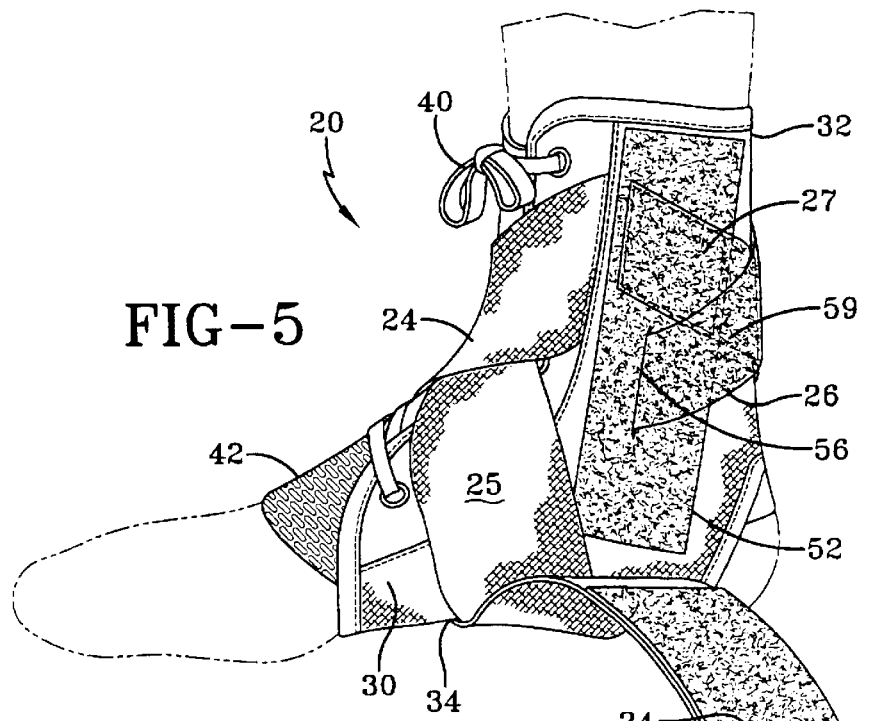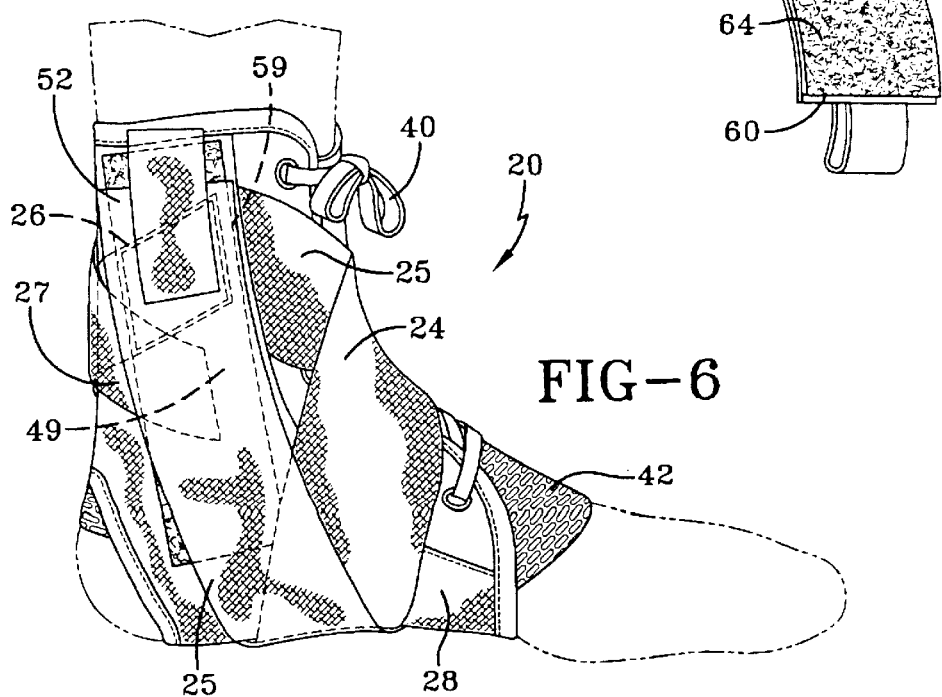

ANKLE BRACE

CROSS-REFERENCE TO RELATED APPLICATIONS (Not applicable)

STATEMENT REGARDING FEDERALLY SPONSORED RESEARCH OR DEVELOPMENT (Not Applicable)

Reference to a "Microfiche Appendix"

(Not Applicable)

BACKGROUND OF THE INVENTION

1. Field of Invention

The present invention relates generally to ankle brace devices which are worn to support the ankle joint as a preventive measure or to aid recovery after injury or surgery.

2. Background of Related Art

The present invention relates to ankle brace devices which are placed and secured upon a human's foot and ankle joint area to support the ankle joint and maintain the ankle joint structures in an appropriate position to enhance healing after injury or surgery or as a preventive measure to minimize injury to a healthy ankle joint.

The use of athletic adhesive tape has long been applied by athletic trainers to provide support to the ankle joint. However, such taping procedures possess certain drawbacks which encouraged prior art attempts to develop a removable and reusable ankle brace in lieu of conventional taping procedures.

There are a multitude of various prior and current available ankle brace designs which are intended to be removably disposed over one's foot and ankle and fastened in place using a "boot-like" or main body portion which includes a lacing arrangement, the well-known "Velcro" type arrangement, or other releasable fastening means.

Some of these prior and currently employed brace arrangements also utilize elongate straps to surround portions of the foot and ankle area to attempt to simulate support similar to that provided by conventional taping procedures employed by athletic trainers to provide a measure of stability and support.

Other versions of removable braces employ relatively rigid components vertically disposed adjacent to the inner and outer sides of the ankle joint and held in place in the form of splints. While many of these prior designs provide a degree of support to the ankle joint, there is a need to provide an improved ankle brace which offers greater positive support to the ankle joint structures most often subjected to injury and yet permit the ankle joint to move within the normal range of motion during activity by the user.

BRIEF SUMMARY OF THE DISCLOSURE

The present invention relates generally to joint braces and particularly to an improved brace for the human ankle joint. In accordance with the present invention, an improved ankle brace is provided which incorporates additional advantages compared to the prior art through a new combination of components providing generally enhanced positive support. The present invention is particularly useful to support the anterior talofibular ligament (ATFL) and the calcaneofibular ligament (CFL) in their anatomically correct alignment relative to the leg and foot bones of the ankle.

In general, the brace incorporating a construction in accordance with the present invention combines restricting the degree of displacement of the ankle bones of the wearer in both vertical and horizontal directions. This provides positive support particularly to the ATFL and CFL ligaments by resisting forces applied to the ankle joint which tend to place undue strain upon these ligaments.

It is well-documented that the most common form of ligament injury due to sprains involve the tearing or complete rupture of the anterior talofibular ligament. Less common is the simultaneous similar damage to the CFL in the more severe ankle sprains. In accordance with the present invention, the location and function of the stabilizing straps forming a portion of the ankle brace .provide an improved degree of positive support to the ATFL and restricts anterior displacement of the talus bone under the fibula which occurs when the ATFL becomes torn or completely ruptured.

A further aspect of a more preferred embodiment of the present invention involves the use of two pair of stabilizing straps attached to a main body portion of the brace. The main body portion is adapted to snugly receive a portion of the wearers foot and cover the ankle area of the foot to provide a degree of compression over the ankle joint area. In accordance with the present invention, the first pair of stabilizing straps, each having one end fixed to an opposing side portion of the main body, wrap around the rear of the ankle area above the heel of the wearer's foot in opposing directions and are releasably fixed to the opposing side. This pair of support straps provide positive support in a horizontal direction.

The second pair of support straps each include an end fixed to a side portion of the main body portion. A free end is wrapped from one side of the ankle joint over the top of the foot, under the sole of the foot and vertically upwardly to be releasably fixed to the same side of the main body portion as its fixed end to provide support in the vertical direction. This second pair of support straps primarily restrict vertical displacement of the tibia and fibula relative to the talus. The combination of the first pair and second pair of support straps, work synergistically to provide increased stability maintaining the ankle joint in an anatomical correct position and yet permit a range of flexure of the ankle within normal limits.

As another aspect of the present invention, the support provided by the two pair of straps described above also provide support for the remaining ligament structures of the ankle joint because the vertical and horizontal stabilization of the ankle joint tends to maintain the normal relationship between the bones which form the joint.

It is another aspect of the present invention to provide an ankle brace of the type described which can be constructed in an efficient manner at reasonable costs relative to prior and current ankle braces available presently and functionally fits either the right or left foot of a wearer.

BRIEF DESCRIPTION OF THE DRAWINGS

FIG. 5 is a right side elevational view of the ankle brace as shown in FIG. 3 with one of the pairs of support straps in a partially wrapped condition;

FIG. 6 is a left side elevational view of the ankle brace as shown in FIG. 3;

Figure 1:
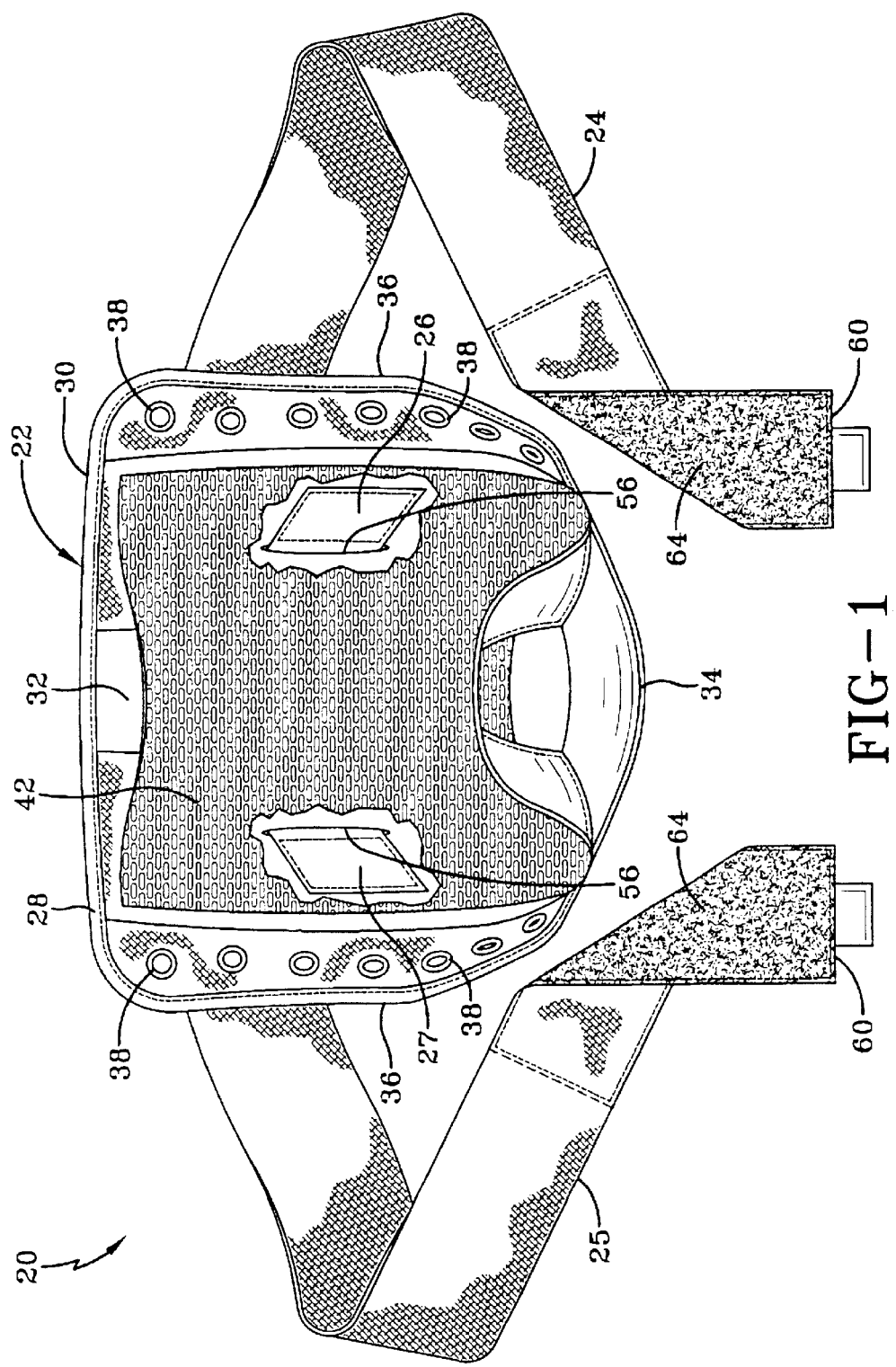
FIG. 1 is a front elevational view of an ankle brace constructed in accordance with the present invention.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose.

DETAILED DESCRIPTION OF THE INVENTION

Figure 2:
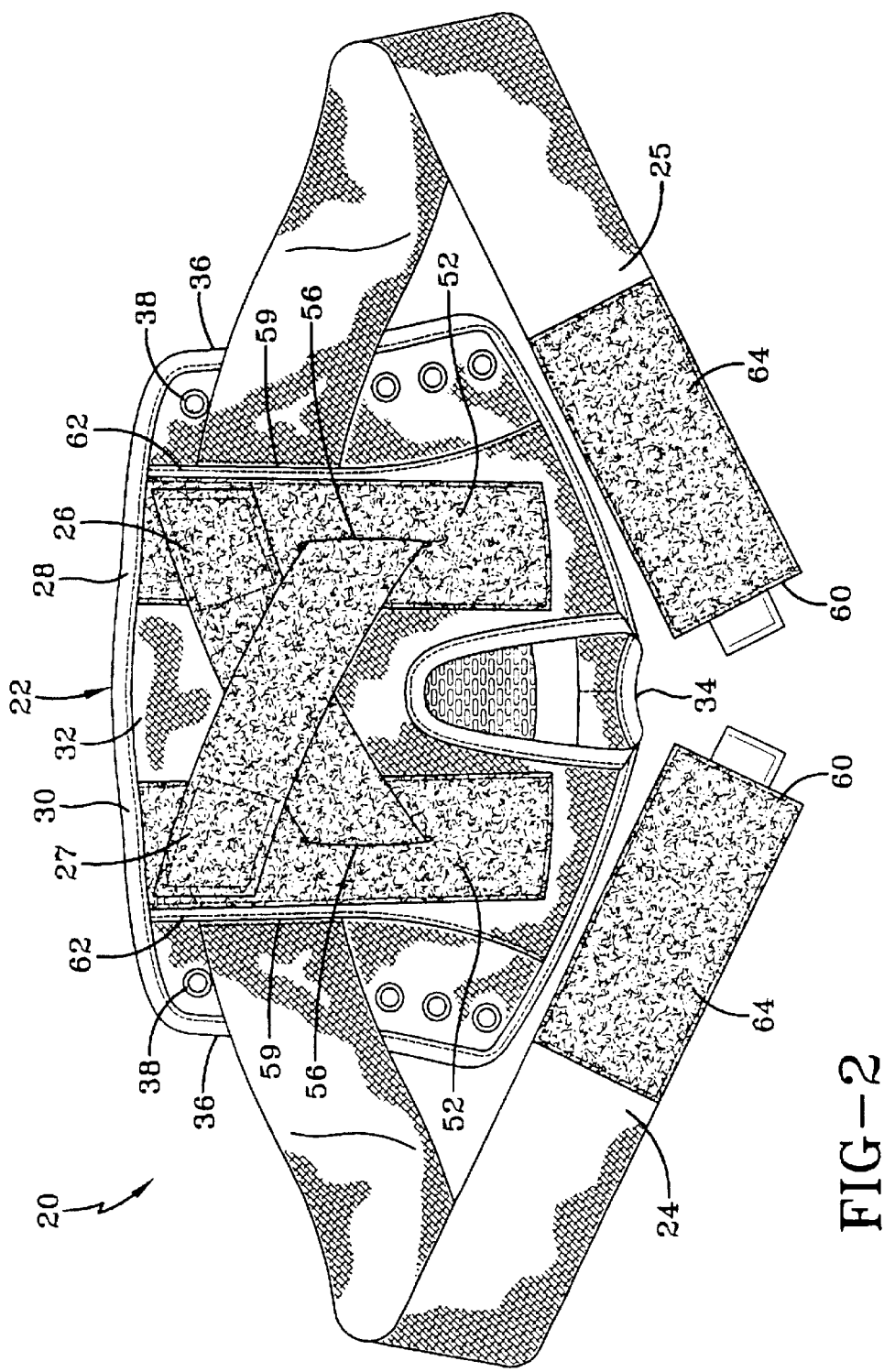
FIG. 2 is a rear elevational view of the ankle brace shown in FIG. 1.

An ankle brace, indicated generally at 20, constructed in accordance with the present invention is illustrated in FIGS. 1 and 2. Brace 20 includes a main body, indicated generally at 22, and two pair of support straps 24, 25, 26 and 27.

Figure 3:
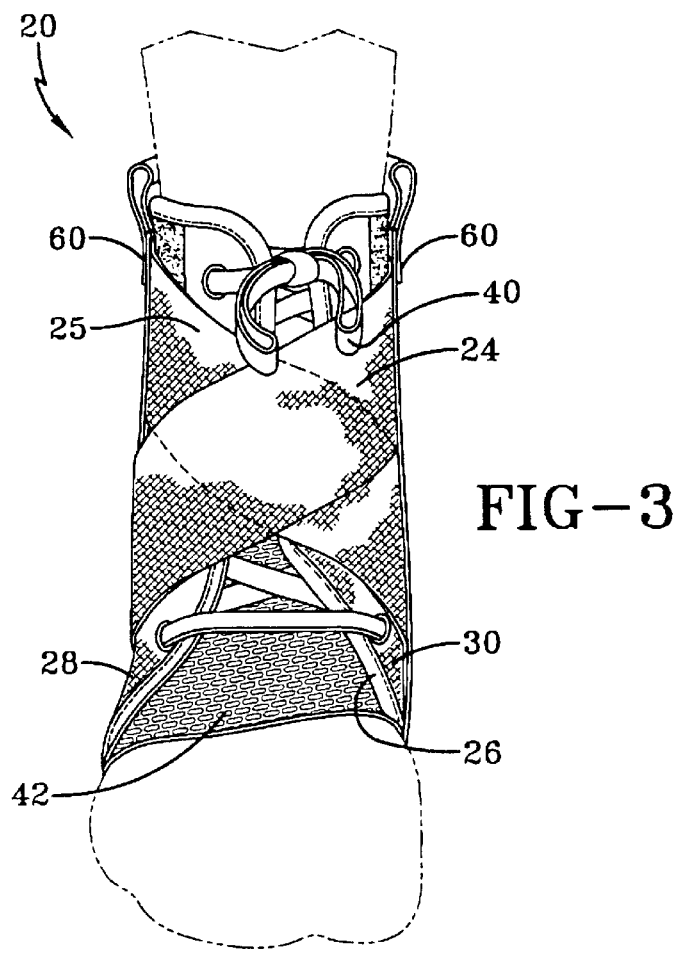
FIG. 3 is a front elevational view of the ankle brace shown in the preceding figures and illustrated in its operative position on a user's foot indicated by ghost lines.
Figure 4:
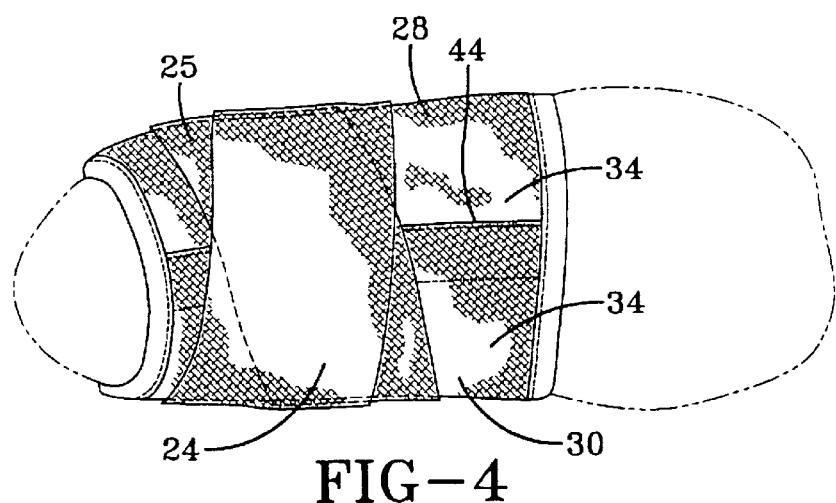
FIG. 4 is a bottom plan view of the ankle brace as shown in FIG. 3.

Main body 22 comprises a flexible, non-elastic or at least minimally elastic, material and includes side sections 28 and 30, a rear section 32, and a bottom section 34, which surround the foot and ankle of the wearer in a shoe or boot-like configuration such as shown in FIGS. 3 and 4. Openings for the toes, forefoot, and heel of the wearer are provided for ease in positioning the main body 22 on the foot to surround the ankle joint area, including a part of the lower leg adjacent thereto. Side sections 28 and 30 extend forwardly from rear section 32 to form adjacently spaced, front edges 36 which are configured to conform to the top of the wearer's foot and to the lower shin area.

Front edges 36 are provided with means for connecting the edges so they may be drawn toward one another to pull main body 22 into a snug fit applying compression upon the wearer's foot and ankle portion. In the preferred embodiment shown in the figures, a plurality of conventional eyelets, such as at 38, are provided to cooperate with a convention shoe-type lace 40 to accomplish this intended purpose. However, other suitable forms of conventional connecting means, such as for example, the well-known hook and loop type fabric fasteners, commonly sold under the trademark "VELCRO", may also be advantageously employed to accomplish this connecting purpose.

A tongue 42 may be secured between the spaced front edges 36 by attachment to an inner surface of one or both of the side sections 28 and 30 in any suitable conventional manner. Tongue 42 primarily provides padding for the comfort of the user upon tightening the shoe-type lace 40.

Side sections 28, 30 and rear section 32 are joined by a sewn seam 44, (FIG. 4) under the midline of the wearer's foot to form bottom section 34 which overlies the arch of the foot. A frontal opening is preferably provided between the side and bottom sections to permit the wearer's forefoot and toes to extend outward of the main body portion 22.

Rear section 32 extends upwardly above the wearer's heel along the Achilles tendon and closely conforms to the configuration of the rearward portion of the ankle and lower shin area of the wearer. A rearward facing opening may be provided to receive the heel portion of the wearer.

Figure 7A:
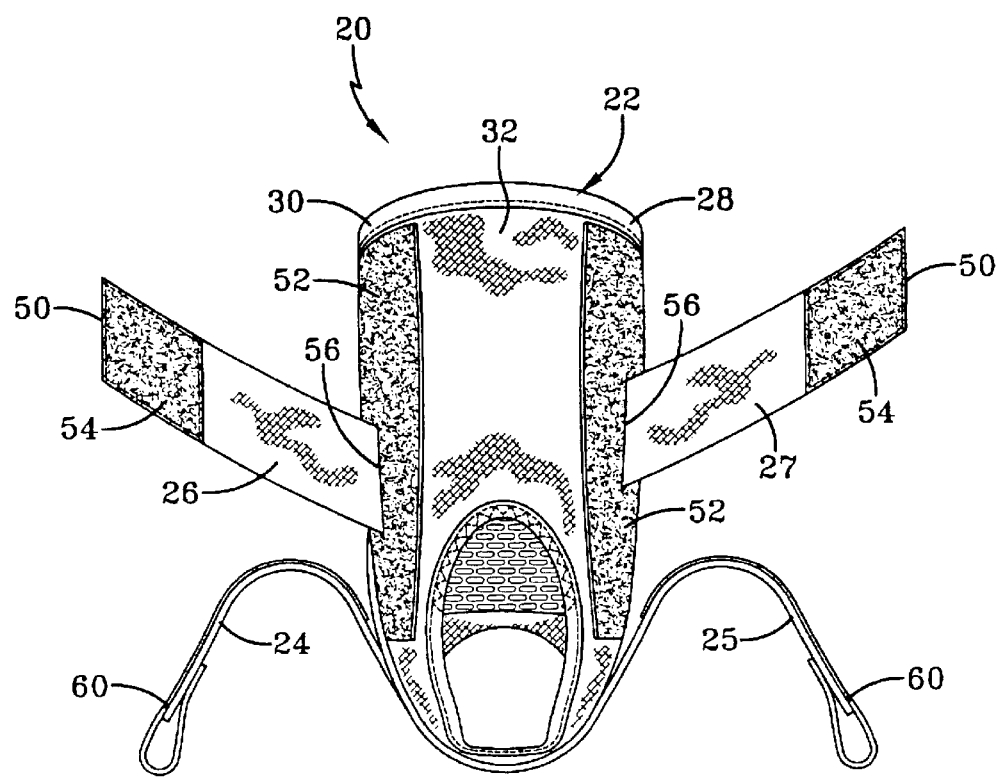
FIGS. 7A through 7C are rear views of the ankle brace shown in the preceding figures illustrating the preferred procedure for wrapping and fixing the other pair of support straps in a functional position upon placing the brace on a user's foot and ankle region.
Figure 7B:
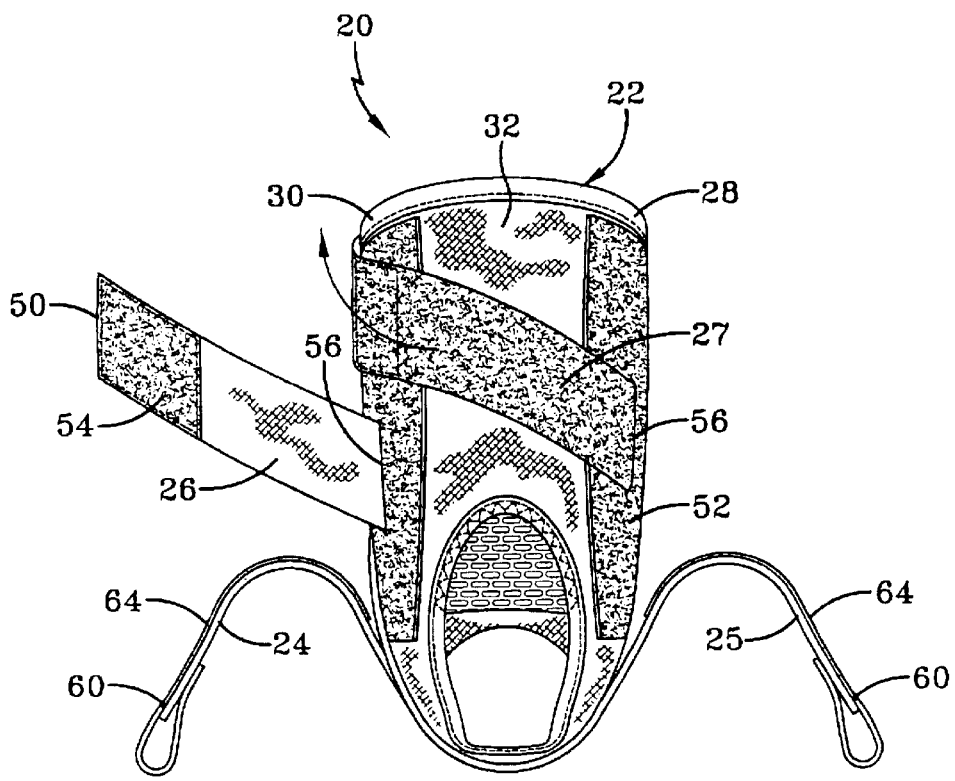
Figure 7C:
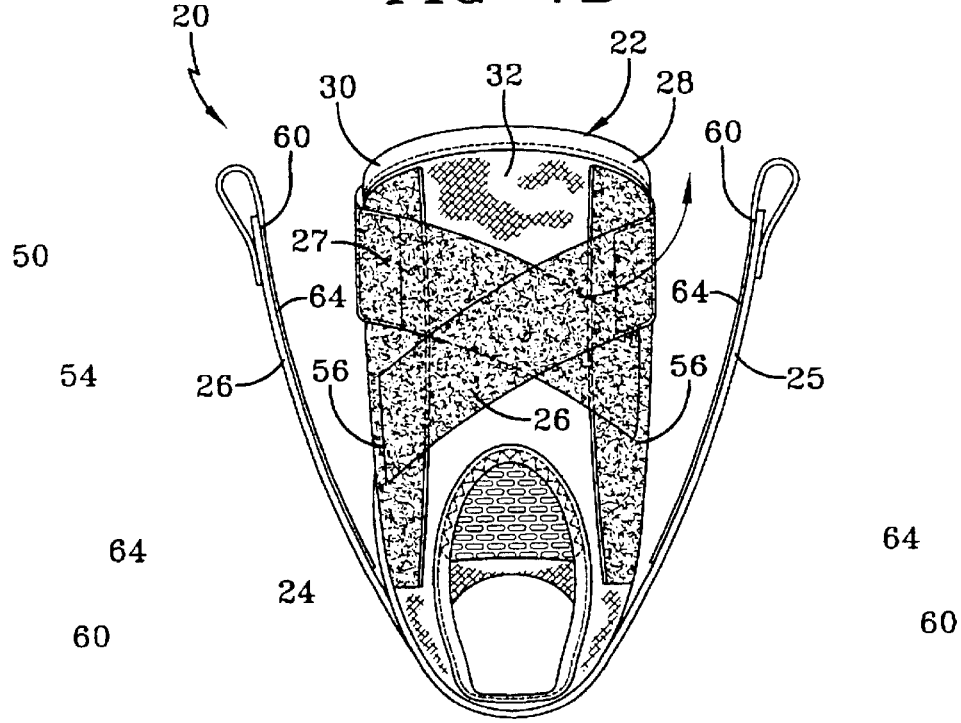
Figure 8A:
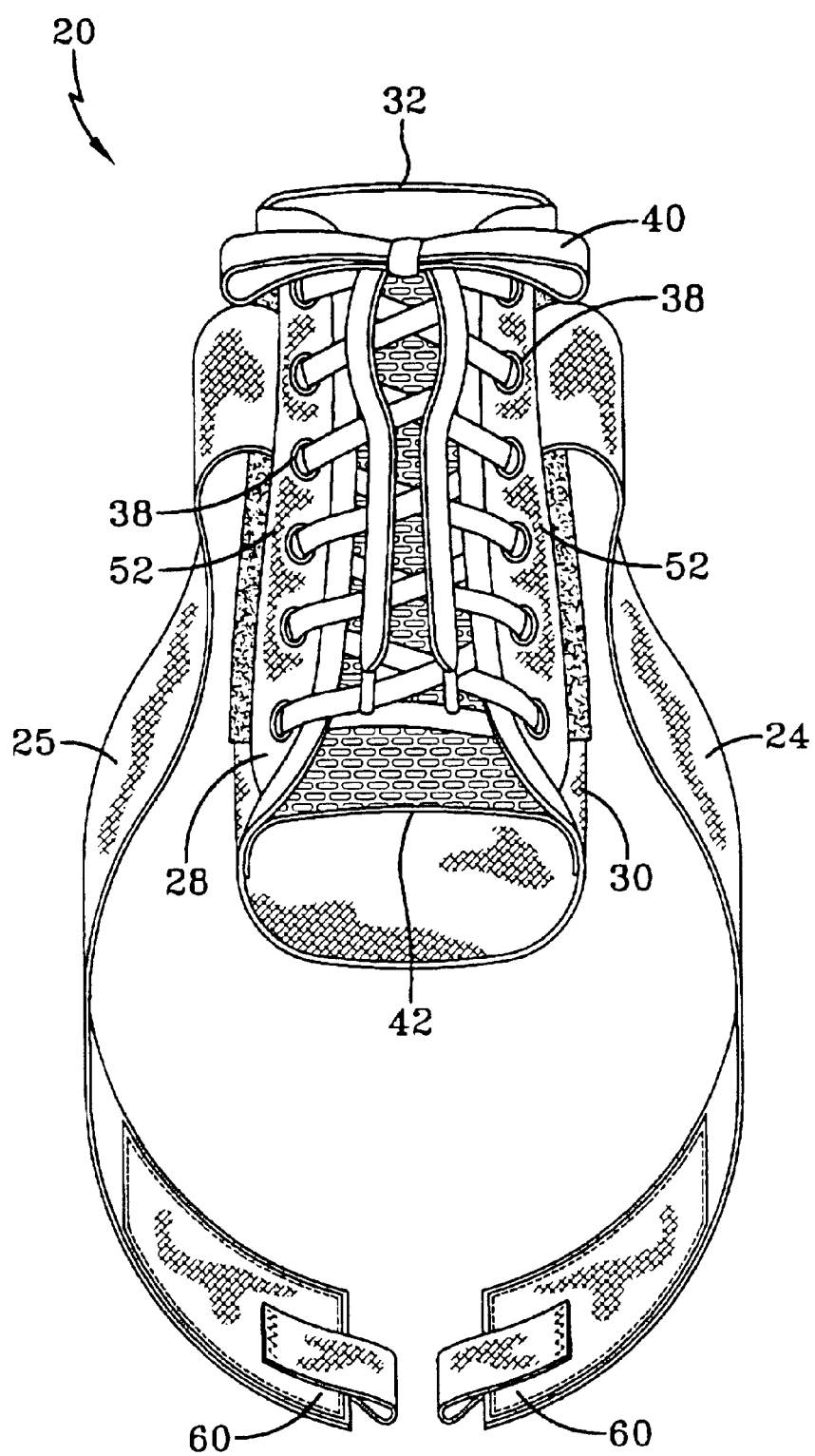
FIGS. 8A through 8C are front views of the ankle brace as shown in FIGS. 7A–7C illustrating the preferred procedure for wrapping and fixing the other pair of support straps in a functional position upon placing the brace on a user's foot and ankle region.
Figure 8B:
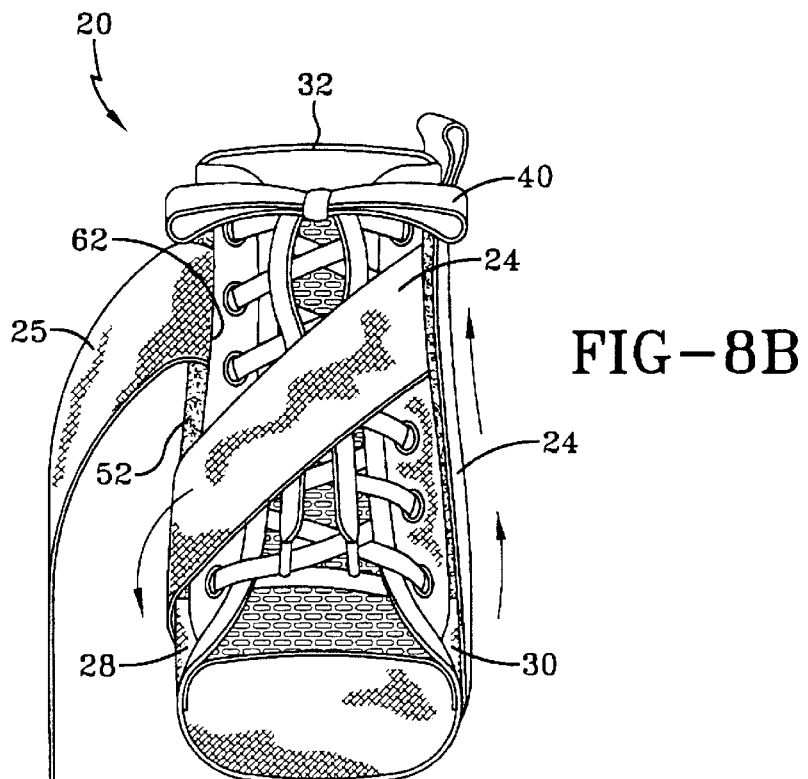
Figure 8C:
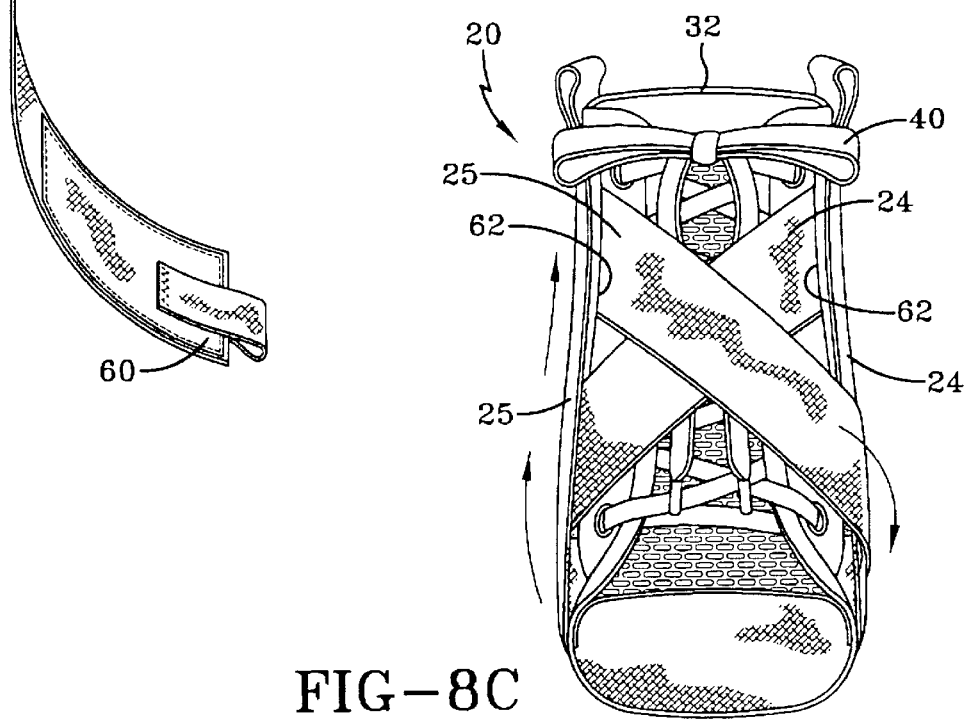

With reference to FIGS. 5–7, support straps 26 and 27 have one end 49 fixed to either the outer or inner surface of a respective side section 28, 30 and a free end 50 which may be extended and wrapped around rear section 32 for releasable attachment to the opposing side section 28 or 30 such as shown in FIGS. 7A through 7C. As best seen in FIGS. 7A–7C, the angle at which a respective strap 26 and 27 wrap around rear section 32 may be adjusted to facilitate one crossing over the other without interference.

A preferred means for releasably attaching the free ends 50 to the opposing side section is the well-known hook and loop type fabric fastener, commonly available under the trademark "Velcro". A strip of such fastening material such as at 52, is sewn or otherwise fixed to an outer surface of each of said side sections 28 and 30 and a cooperating strip 54 of such fastening material is fixed to an inwardly facing surface adjacent to the free end 50 of each strap 26 and 27.

As shown in a preferred embodiment in FIGS. 1 and 7A and 7B, the fixed ends 49 of straps 26 and 27 are attached to an inner surface of a respective one of side section 28 or 30 and extend outwardly through a slit-like opening 56 provided in a respective side section 28 or 30. In the preferred embodiment shown, the fixed ends 49 are sewn to a respective inner surface of side sections 28 or 30 near but spaced from eyelets 38. Other equivalent fixing means could be used to obtain a secure attachment. It should also be noted that the fixed ends of straps 26 and 27 may be similarly attached to an outer surface of the side sections 28 and 30 to obtain an equivalent function and result in accordance with the present invention.

Straps 26 and 27 are positioned so that the free ends may extend around the rear section 32 above the heel of the wearer and be releasably fixed to the opposite side section 28, 30 at a location preferably above the malleoli of the wearer.

In an operative position, support straps 26 and 27 function to provide support to the ankle joint primarily in a horizontal direction along the medial and lateral sides of the ankle joint to aid in maintaining the fibula and tibia in their anatomically correct relationship to one another.

As noted earlier herein, the most common ligament damage occurs in the inversion-type injury of the ankle joint and involves the anterior talofibular ligament (ATFL). It has been estimated that as high as sixty-five percent of ankle sprains involved damage the ATFL. This ligament is located on the lateral or outer side of the ankle joint and is connected to the end of the fibula and the talus of the foot.

When the ATFL is sprained to a degree that instability of the ankle joint is present, such instability manifests itself by anterior subluxation of the talus. This is often diagnosed by the commonly referred to "drawer test". In this test, the lower area of the shin is held or pushed rearwardly and a horizontal force in a forward direction is applied to heel of the foot. If the ATFL is significantly torn or completely torn, this test reveals a significant degree of anterior displacement of the talus.

Straps 26 and 27 provide significant support in the horizontal direction when positioned as described to aid in maintaining the fibula and talus in their normal horizontal relationship. This horizontal restraint also provides support to all ligament structures which possess a function related to the correct horizontal position of the bones comprising the ankle joint.

Another advantage of providing two opposing straps 26 and 27 is that the ankle brace 20 of the present invention equally fits and functions on either the left or right foot of the wearer such that the ATFL is duly supported by restraining anterior displacement of the talus.

The other pair of support straps 24, 25 each include a fixed end 59 sewn or otherwise attached to a respective outer surface of side sections 28 and 30 along a seam 62 and include a free end 60 as shown in FIGS. 1 and 2. Preferably the free end 60 has a strip 64 of the previously described hook and loop type fabric fastening means attached to the area adjacent free end 60. Fixed ends 59 are attached to a respective side section 28 or 30 at a location near the upper portion thereof so that free ends 60 are extendable downwardly over the top of the wearer's foot and under the arch, and then vertically for releasably fix fabric strip 64 to fabric strip 52 disposed on the same one of side sections 28 or 30 as its respective fixed end 59, such as illustrated in drawing figures.

In the preferred embodiment shown, support straps 26 and 27 are preferably positioned first and may include an outwardly facing surface having a fabric covering 55 provided with the same fabric structure as strip 52. Then cooperating fabric strip 64 on a respective strap 26, 27 may be secured to both the strip 52 as well as to an exposed underlying portion 55 of straps 27, 28. In this configuration the free ends 60 of each strap 24 or 25 are securely and releasably fixed to a respective side section 28 or 30.

To use the ankle brace of the present invention, the main body portion 22 may be placed on either of the wearer's foot in a conventional fashion by inserting the toes and forefoot through the frontal opening with the heel extending through the opening in rear section 32. The tongue 42 is positioned over the instep and front ankle area in a conventional manner and then the lace 40 may be drawn tight and conventionally tied, see FIG. 3. Appropriately positioning and tightening the lace 40 assures main body 22 is snugly fitted over the foot and ankle portion as shown.

The support straps 26 and 27, in either order, may then be extended around rear section 32 and drawn tightly with the respective free end 50 releasably fixed to the opposite side section 28 or 30 via the fastening means 54 and 52 as described above herein.

Next, support straps 24 and 25 are positioned as shown in FIGS. 8A through 8C and FIGS. 5 and 6. In either order, one of each strap 24 or 25 is extended downwardly over the top of the wearer's foot, then under the arch and then upwardly in a vertical manner for releasable attachment of free end 60 to the same side section 28 or 30 as its respective fixed end 59. The other of these straps is then extended in the opposing direction and attached in the same manner, overlapping one another on the instep and arch of the user.

While the support straps 26 and 27 may be drawn around the rear section 32 in either order and obtain good results, it is preferred that the strap 26 or 27 which is fixed to the lateral side of the foot is positioned first. Which of the straps 26 or 27 is applicable in this regard depends upon whether the brace 20 is applied to the left or right foot.

The preferred order of placement of straps 26, 27 referred to above applies a primarily horizontally directed force drawing the fibula and talus toward one another to restore or stabilize their proper anatomical relationship. However, it is important to note that the opposing strap 26 or 27, which is positioned next, tends to balance the force applied by the initially disposed strap, to better assure a more anatomically correct relationship is achieves Additionally, the second one of straps 26 or 27 increases the applied stabilizing forces to maintain the desired position between the fibula and talus bones.

This preferred order of placement of straps 26, 27 in combination with the forces applied by straps 24 and 25, is particularly beneficial in the treatment of an injury or following surgery to either or both the ATFL and CFL. Without appropriate treatment and stabilization, a stretched or partially torn or a newly surgically repaired ligament will tend to heal or repair itself in an elongated state relative to its normal length if the anatomically correct relationship of the involved bones is not maintained. This subsequently leads to a degree of undesirable laxity in the joint increasing instability. This increased instability often leads to further injury to or degradation of related joint tissues and an increased risk of further sprains and/or decreased functionality of the joint.

The use of the ankle brace of the present invention in the treatment of a sprained ATFL and/or CFL has a significantly improved ability to stabilize the tibia and talus in their proper alignment. In turn, this significantly benefits healing of the injured ligament in or very close to its original length. Promoting desirable healing of the involved ligaments in this regard, results in improved stability of the ankle joint more closely duplicating the original degree of joint stability prior to injury.

It is pointed out that support straps 24 and 25 provide support for the ankle joint primarily in a vertical direction tending to maintain the bones of the ankle joint in their normal vertical alignment. In combination and in cooperation with the horizontal support provided by straps 26 and 27, the ankle joint is anchored in both horizontal and vertical directions to stabilize the desired relationship between the bones of the joint and provide balanced support to the ligaments involved.

The positive horizontal and vertical support anchoring the ankle bones in their normal anatomical relationship provides direct support to the calcaneofibular ligament (CFL) in addition to the ATFL. The CFL is comparatively less often injured significantly relative to the ATFL, except in the more serious degrees of inversion sprains. However, in such instances, wearing the brace of the present invention provides very significant support which tends to minimize injury or serious damage to this ligament when the ankle is stressed by undue forces.

While it has been noted that straps 24, 25 primarily provide support by restraining undue vertical displacement and straps 26, 27 primarily provide support by restraining undue horizontal displacement of the ankle joint structure, it should be noted that each pair of straps also provide a component of secondary support in the horizontal and vertical directions complimenting their primary direction of support. The cooperating combination of the two pair of straps located, as described, therefore provide an improved capacity to resist undue stresses which may occur to the ligament structures at various angles during inversion or eversion type sprains wherein a combination of horizontal and vertical components of force are applied to the ankle joint.

It is pointed out that a less preferred embodiment of the present invention may include only one support strap 26 or 27 and provide good results to the user in combination with straps 24 and 25. If only one support strap 26 or 27 is employed, it is recommended that it be fixed to the lateral side section of the main body 22 and drawn around the heel as described for releasably fixing to the medial side section.

The lateral or medial side will depend upon whether the brace is applied to the left or right foot, therefore such a construction would not be universal to either foot as the more preferred embodiment described herein, nor provide the increased stabilizing forces obtained by employing both straps 26 and 27 as described herein.

Prior ankle braces have employed straps at various locations in combination with a boot-like main body portion, however, they have not satisfactorily provided the degree of support in both the horizontal and vertical directions as compared to the brace of the present invention. Therefore, the benefits provided by prior removable braces to the complex relationship between the ankle joint structures, while providing some benefits, have fallen short of the most desired results.

In view of the foregoing description, it should be understood that the brace of the present invention provides improved support and stability in a construction which is of comparable cost and as convenient to wear as compared to the prior art removable ankle braces.

The benefits of the ankle brace of the present invention extend to both use during a rehabilitation period after injury or surgery as well as a measure to prevent or reduce the degree of damage caused by an undue strains upon an uninjured ankle joint.

While certain preferred embodiments of the present invention have been disclosed in detail, it is to be understood that various modifications may be adopted without departing from the spirit of the invention or scope of the following claims.

What is claimed is:

1. A brace for supporting the ankle joint, comprising:
   a) a main body of flexible sheet material configured to receive the ankle portion of a wearer's foot in overlying relationship to medial, lateral and rear portions of the ankle area and under a portion of the wearer's foot, said main body including medial and lateral side sections and a rear section extending around and upwardly above the ankle joint, said side sections including opposing frontal edges extending along substantially the length of said main body;
   b) connecting means associated with said frontal edges for drawing said side sections toward one another to secure said main body in a close-fitting relationship with the underlying ankle and foot portions of the wearer;
   c) a first pair of elongate support straps, one of said support straps having an end portion fixed to the medial section of said main body portion and a free end extendable downwardly over a portion of the wearer's foot and under the arch of the wearer and then upwardly for removable attachment to the medial side section of said main body above the malleoli of the wearer; the other of said first pair of support straps having an end portion fixed to the lateral side section of said main body and a free end extendable downwardly over an upper portion of the wearer's foot and under the arch of the wearer's foot, and then upwardly for removable attachment to the lateral side section of said main body above the malleoli of the wearer; and
   d) a second pair of elongate support straps;
   i) one of said second pair having one end portion fixed to said medial side section of said main body and an opposing end extended in tension around the rear of the wearer's foot above the heel and attached to the lateral side section of said main body at an angle relative to the malleoli of the wearer to substantially inhibit anterior motion of the talus relative to the lower end of the fibula;
   ii) the other of said second pair having an end portion fixed to said lateral side section of said main body and an opposing end extended in tension around the rear of the wearer's foot above the heel and attached to the medial side section of said main body portion at a location relative to the malleoli of the wearer to complement the inhibition of anterior motion applied by said strap recited in paragraph (d)(i).

2. In a removably mounted brace for supporting the ankle joint of the type having a main body portion of flexible material configured to be received in surrounding relationship by foot and ankle portions of the wearer, said main body portion including medial and lateral side sections, a rear section and connecting means for drawing said side and rear sections into close-fitting relationship with the underlying portions of the foot and ankle portions of the wearer, the combination of:
   a) a first pair of support straps, a respective one having an end fixed to one of said lateral or medial side sections and a free end extendable around the rear section and releasably fixed to the opposite side section relative to the malleoli of the wearer to apply a primary horizontally directed force drawing the fibula and talus toward one another to substantially restrain anterior motion of the talus relative to the lower end of the fibula; and
   b) a second pair of support straps, a respective one having a fixed end mounted to one of said lateral or medial side sections and a free end extendable downwardly over a portion of the instep of the wearer's foot and under the arch and then vertically for releasable attachment to the same side section as its fixed end; wherein said first and second pair of support straps in their operative fixed position cooperate to restrain both vertical and horizontal displacement of the lower ends of the fibula and tibia from their normal anatomical relationship to the talus.

3. In a removably mounted brace for supporting the ankle joint of the type having a main body portion of flexible material configured to be received in surrounding relationship to the foot and ankle portions of the wearer, said main body portion including medial and lateral side sections, a rear section and connecting means for drawing said side and rear sections into close-fitting relationship with the underlying portions of the foot and ankle portions of the wearer, the combination of:
   a) at least one first support strap having an end fixed to said lateral side section and a free end extendable around the rear section and releasably fixed to the medial side section relative to the malleoli of the wearer to apply a primarily horizontally directed force drawing the fibula and talus toward one another to substantially restrain anterior motion of the talus relative to the lower end of the fibula;
   b) a pair of second support straps, a respective one having a fixed end mounted to one of said lateral or medial side sections and a free end extendable downwardly over a portion of the instep of the wearer's foot and under the arch and then vertically for releasable attachment to the same side section as its fixed end; wherein said first and second support straps in their operative fixed position cooperate to restrain both vertical and horizontal displacement of the lower ends of the fibula and tibia beyond their normal anatomical relationship to the talus.

* * * * *